United States Patent [19]

Holmes et al.

[11] Patent Number: 4,910,145
[45] Date of Patent: Mar. 20, 1990

[54] SEPARATION PROCESS

[75] Inventors: Paul A. Holmes, Northallerton; Guan B. Lim, Stockton-on-Tees, both of United Kingdom

[73] Assignee: Imperial Chemical Industries PLC, London, United Kingdom

[21] Appl. No.: 374,567

[22] Filed: Jun. 30, 1989

Related U.S. Application Data

[63] Continuation of Ser. No. 161,369, Feb. 22, 1988, abandoned, which is a continuation of Ser. No. 668,020, Nov. 5, 1984, abandoned.

[30] Foreign Application Priority Data

Nov. 23, 1983 [GB] United Kingdom ............... 8331199
May 8, 1984 [GB] United Kingdom ............... 8411670

[51] Int. Cl.$^4$ ................... C12N 1/06; C12P 7/52; C12P 7/64
[52] U.S. Cl. ................... 435/259; 435/134; 435/141; 435/271; 435/829; 435/874
[58] Field of Search ............ 435/135, 136, 141, 134, 435/259, 262, 271

[56] References Cited

U.S. PATENT DOCUMENTS

| | | | |
|---|---|---|---|
| 3,275,610 | 9/1966 | Coty | 260/80 |
| 3,928,642 | 12/1975 | Hubert et al. | 426/521 |
| 4,138,291 | 2/1979 | Lafferty | 195/47 |
| 4,358,583 | 11/1982 | Walker et al. | 528/491 |
| 4,562,245 | 12/1985 | Stageman | 528/361 |

FOREIGN PATENT DOCUMENTS

| | | |
|---|---|---|
| 659731 | 5/1965 | Belgium . |
| 0046017 | 2/1982 | European Pat. Off. . |
| 0046335 | 2/1982 | European Pat. Off. . |
| 0061250 | 9/1982 | European Pat. Off. . |
| 0078556 | 5/1983 | European Pat. Off. . |
| 0114086 | 7/1984 | European Pat. Off. . |
| 2273067 | 12/1975 | France . |

OTHER PUBLICATIONS

Krieg et al. eds. In *Bergey's Manual of Systematic Bacteriology*, 9th Ed., vol. pp. 34–35.
Merrick et al. Journal of Bacteriology (1964), vol. 88, No. 1, pp. 60–71, Schlegel Allugemeine Microbiologie, Georg Thiene Verlag Stuttgart (1976), p. 38, FIG. 25, Martin et al., Zeit. for Naturforschung, (1962), 17b, pp. 190–196.
Braun et European J. Biochem. (1969) 10: 426–438.
Biochemistry, vol. 7, No. 10, Oct. 1986, pp. 3676–3681; R. Griebel et al.; "Metabolism of Poly–Beta–Hydroxybutyrate., I. Purification, Composition, and Properties of Native Poly–Beta–Hydroxybutyrate Granules from Bacillus Megaterium".
List of Products—Nova.

*Primary Examiner*—Thomas D. Mays
*Attorney, Agent, or Firm*—Cushman, Darby & Cushman

[57] ABSTRACT

An aqueous suspension of micro-organism cells containing a 3-hydroxybutyrate polymer are subjected to a proteolytic enzyme digestion and/or a surfactant digestion in order to solubilise cell material other than the 3-hydroxybutyrate polymer.

Prior to, or during the digestion, but before any proteolytic enzyme digestion step, the suspension is heated to at least 80° C. to denature nucleic acids which otherwise hinder separation of the 3-hydroxybutyrate polymer containing residue from the suspension.

10 Claims, No Drawings

SEPARATION PROCESS

This is a continuation of application Ser. No. 07/161,369, filed Feb. 22, 1988, which was abandoned upon the filing hereof, and which was itself a continuation of application Ser. No. 06/668,020, filed Nov. 5, 1984 and also now abandoned.

This invention relates to a separation process and in particular to the separation of 3-hydroxybutyrate polymers from micro-organisms.

Poly(3-hydroxybutyrate) is a thermoplastic polyester consisting of repeat units of the formula $$-CH(CH_3).CH_2.CO.O-$$

which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in EP-A-15669 and 46344.

Polymers containing both 3-hydroxybutyrate units and other hydroxycarboxylic acid units, such as 3-hydroxyvalerate units, can also be produced microbiologically. Thus a microbiologically produced heteropolymer containing 3-hydroxybutyrate and 3-hydroxyvalerate residues is described by Wallen et al in "Environmental Science and Technology" 8 (1974) 576–9. Also, as described in EP-A-52459 and 69497 various copolymers can be produced by cultivating the micro-organism on certain substrates, such as propionic acid which gives rise to 3-hydroxyvalerate units in the copolymer.

Accordingly, in the present specification, by the term HB polymer we mean not only the homopolymer, poly(3-hydroxybutyrate), but also copolymers as described above, provided that the 3-hydroxybutyrate residues form at least 40 mol %, and preferably at least 50, mol % of the polymer chain.

While cells containing the polymer can be used as such as a moulding material, for example as described in US-A-3107172, it is generally desirable to separate the polymer from the remainder of the cell material.

The majority of the separation processes that have heretofore been proposed involves extraction of the polymer from the cells with a solvent in which the HB polymer is soluble, followed by separation of the polymer solution, hereinafter termed a syrup, from the cell residue. Generally such an extraction step is effected after the cells have been subjected to a treatment, e.g. milling, spray drying, that renders the cells permeable to the extraction solvent; typical solvent extraction processes are described in EP-A-15123.

The separation of the syrup from the cell residue is normally effected by filtration or centrifugation: however syrups containing more than about 5% by weight of polymer tend to be very viscous thereby rendering such filtration or centrifugation steps difficult, particularly where the proportion of non-HB polymer cell material (hereinafter termed NPCM) to be separated is considerable. The proportion of NPCM to be separated will of course depend on the HB polymer content of the micro-organism cells.

While there have been reports in the literature of micro-organism cells containing large proportions of HB polymer, economic considerations of the cultivation procedure often limit the proportion of HB polymer in the micro-organism cells, necessitating the use of large amounts of extraction solvents in order that the syrups are sufficiently dilute to enable easy separation of the NPCM from the syrup. Not only does the use of such dilute syrups necessitate the use of large vessels and involve large solvent recovery costs but also a considerable solvent loss is liable to occur, even when a relatively efficient solvent recovery procedure is employed. Thus, if a syrup concentration of 5% by weight is employed, even if 95% by weight of the solvent is recovered for re-use, to extract 1 kg of polymer, 1 kg of solvent is lost: with syrups of lower concentrations and/or less efficient solvent recovery procedures, the amount of solvent lost is even greater. Thus, in addition to the extraction processing, including solvent recovery, costs, such an extraction process thus involves a significant raw material cost, viz the cost of the unrecovered solvent, on top of the cost of producing the polymer.

In the above extraction process, the HB polymer is extracted by dissolution in a solvent leaving NPCM undissolved. However some of the NPCM, e.g. lipids, may also be soluble in the solvent used for extraction of the HB polymer and so be present in the syrup. Hence if it is desired to obtain an HB polymer product free of such dissolved NPCM "impurities", either a preliminary extraction step with a solvent in which the HB polymer is not soluble is required to remove the HB polymer-extraction solvent soluble "impurities" prior to extraction of the HB polymer, or else the HB polymer has to be selectively separated from the syrup, e.g. by precipitation. The adoption of selective separation steps, e.g. precipitation, often further complicates solvent recovery procedures.

We have now devised a process where in the bulk of the NPCM can be separated from the HB polymer without incurring such large solvent losses with their consequent raw material costs.

In the present invention a substantial proportion of the NPCM is solubilised, preferably enzymatically, leaving the HB polymer undissolved.

Thus in the present invention the reverse procedure is adopted, viz dissolution of NPCM, i.e. the "impurities", leaving the HB polymer undissolved. The dissolution of NPCM may be effected in several stages so that it is possible to obtain HB polymer products of progressively increasing purity. Of course the more stages involved, the higher the cost of the procedure. Since, for some applications of HB polymer products, a less pure product can be tolerated than is required for other applications, it is seen that by extracting the "impurities" progressively, such tolerable, less pure, products can be produced more cheaply, than products of higher purity.

It has been proposed in J. Gen. Microbiology 19 (1958) p. 198–209 to separate the polymer from the micro-organism cells by treatment of the cells with an alkaline sodium hypochlorite solution. While this treatment effects solubilisation of NPCM we have found that, at the same time it causes severe degradation of the HB polymer, rendering the latter unsuitable for many applications.

It has also been proposed in various academic studies of HB polymers, e.g. J. Bacteriology 88, 1 July 1964 pages 60–71 at page 61 to separate the polymer granules from micro-organism cells by suspending the cells in a solution containing lysozyme and deoxyribonuclease, subjecting the suspension to sonication followed by separation of the granules from the cell debris by centrifugation of the suspension layered on to glycerol. However not only are such enzymes relatively expensive and the process not amenable to large scale operation but only a relatively small proportion of the NPCM is solubilised.

According to the present invention we provide a process for the removal of NPCM from micro-organism cells containing an HB polymer comprising digesting an aqueous suspension of said micro-organism cells with at least one solubilising agent whereby NPCM in said cells is solubilised and then separating the insoluble residue containing the HB polymer from the suspension; characterised in that the digestion step includes one or more stages wherein the solubilising agent is a proteolytic enzyme composition and/or a surfactant and said suspension is heated to a temperature above 80° C. before or during said digestion step and before any proteolytic enzyme digestion stage.

Preferably the heating and digestion stages are sufficient to solubilise at least 50% by weight of the NPCM in the original cells and to produce an insoluble residue having an HB polymer content of at least 70% by weight.

The NPCM will generally comprise nucleic acids, lipids and phospholipids, peptidoglycan, proteinaceous materials including glycoproteins and, in some cases lipopolysaccharides and other carbohydrates. The proteinaceous materials generally form at least 40% by weight of the NPCM.

In the process of the invention at least some of the above components of the NPCM are solubilised. This is effected by digesting the cells in one or more stages with a solubilising agent. In at least one stage the solubilising agent is preferably an enzyme composition, and preferably the digestion step involves at least one stage wherein the suspension is treated with a proteolytic enzyme such as pepsin, trypsin, bromelain, papain, facin, rennin, chymotrypsin, and bacterial or fungal proteolytic enzymes or mixtures thereof. Suitable enzyme compositions are those commonly employed in "biological" washing powders.

In at least one digestion stage the solubilising agent is a proteolytic enzyme and/or a surfactant, particularly an anionic surfactant.

Prior to, or during the digestion step, but before any proteolytic enzyme digestion stage, the cells are subjected to a temperature above 80° C. Such a heating step causes denaturing and solubilisation of some of the nucleic acids in the cells: omission of such a heating step precludes satisfactory separation of the insoluble residue after a proteolytic enzyme digestion step, since, in the absence of such a preliminary heating step, the nucleic acids are released from the cells, giving a very viscous suspension, when the cells are digested with a proteolytic enzyme. While such nucleic acids could be solubilised by the addition of de-oxyribonuclease before treatment with the proteolytic enzyme, high concentrations of de-oxyribonuclease, which is relatively expensive, are required. Likewise treatment with de-oxyribonuclease after treatment with a proteolytic enzyme is impractical because of the difficulty of mixing the de-oxyribonuclease with the viscous suspension.

Where the digestion step includes digestion with a proteolytic enzyme, preferably the suspension is heated to a temperature above 100° C., particularly to above 120° C. under sufficient superatmospheric pressure to maintain the aqueous medium in the liquid state and then the pressure is reduced, for example by extruding the heated suspension into a region maintained at a pressure at which the aqueous medium volatilises, or by simply cooling the suspension.

The duration of the heat treatment that is required to effect solubilisation and de-naturing of nucleic acids will vary with the temperature employed. Thus the requisite duration will decrease as the temperature to which the suspension is subject increases. While heating for at least 5 minutes, and preferably at least 10 minutes, may be required at temperatures of about 100° C., much shorter periods can be employed at higher temperatures: for example at 150° C., heating periods as short as 20 sec. can be used. Any digestion stage employing a surfactant as the solubilisation agent will normally be conducted at temperatures above 80° C. in order to effect rapid solubilisation by the surfactant.

Although a wide range of pH conditions can be employed for the heating step to affect denaturing and solubilisation of the nucleic acids, the conditions are preferably near neutral, e.g. pH 6–8, to minimise the risk of degradation of the HB polymer.

In a preferred form of the invention as mentioned hereinbefore, at least part of the solubilisation is effected by digesting the cells with an enzyme composition, in particular by employing at least one digestion stage wherein the solubilising agent is a proteolytic enzyme composition.

Since many enzyme compositions tend to be denatured at temperatures above 60° C., the heating step to denature and solubilise nucleic acids is carried out prior to treatment with the enzyme composition.

If an enzyme digestion step is employed, the digestion should be conducted at a temperature below that at which the enzyme is denatured. In many cases the denaturing temperature will be below 65° C. but with some enzymes the denaturing temperature is higher and so, with such enzymes, digestion temperatures above 65° C. can be employed. It is preferred that the digestion temperature is below 80° C. Except possibly for enzymes that can tolerate temperatures above 60° C., the digestion is preferably conducted at a temperature below 60° C., particularly at a temperature in the range 50° to 60° C. Since, when using an enzyme digestion step, the suspension is normally heated to a temperature above that employed in the enzyme digestion stage, cooling of the cells will generally be necessary prior to enzyme digestion. The cells may be separated from the heated suspension, e.g. by filtration or centrifugation, and then resuspended in another aqueous medium: alternatively the heated suspension may simply be cooled to the required digestion temperature and the enzymatic digestion step effected thereon.

The solubilised NPCM resulting from enzyme digestion can be used, if desired, as part of the substrate for the cultivation of a further amount of the HB polymer-containing micro-organism thus effecting a saving on the raw material costs in producing the HB polymer-containing micro-organism. The enzymatically solubilised NPCM may be recycled to the fermentation process (after such treatment, e.g. sterilisation, that may be necessary).

Consequently it is preferred that solubilisation is affected enzymatically. Further solubilisation of NPCM in the residue remaining after enzyme digestion may be effected using a surfactant as solubilising agent.

Where solubilisation is carried out using both a proteolytic enzyme composition and a surfactant as solubilisation agents, the digestion is preferably performed in stages with the surfactant digestion stage performed after the enzyme digestion stage or stages. The reason for this preference are two-fold. Firstly, the enzyme composition may be de-activated by the surfactant, secondly, if it is desired to recycle solubilised NPCM to the fermentation step used to produce the micro-organism suspension, the presence of surfactant in the solubilised portion of the suspension may preclude such use.

In order to obtain sufficient, or further, solubilisation of the NPCM, the digestion step may include digestion with a phospholipase enzyme to solubilise phospholipids which generally account for about 6 to 10% by weight of the NPCM of the original cells.

Enzyme digestion is preferably effected by maintaining the cell suspension, to which the enzyme composition has been added, at the requisite temperature and at a pH within the range 6.5 to 9.0 until the requisite degree of treatment has been achieved: this will normally take between 0.2 and 2 hours.

The enzyme digestion may be performed in stages, e.g. an initial treatment with one enzyme composition followed by one or more treatment stages wherein the same or a different enzyme composition is employed. However, it may be convenient, when more than one enzyme is to be used, to treat the cells with an enzyme mixture in a single stage.

Indeed we have found that in some cases a synergistic effect is obtained using an enzyme mixture: thus providing the enzymes do not digest one another, in some cases the use of an enzyme mixture results in a higher degree of solubilisation of NPCM than if the enzymes are used alone or sequentially.

The amount of enzyme, e.g. proteolytic enzyme and/or phospholipase enzyme, required will depend on the nature and activity of the enzyme: typically the amount of proteolytic enzyme composition will be such as to provide 0.5 to 10, preferably 1 to 6, Anson units (AU) of enzyme per 100 g of NPCM in the original cells.

The activity of a proteolytic enzyme may be determined by digesting denatured haemoglobin with the enzyme for 10 minutes at 25° C. and pH 7.5. One Anson unit is the amount of enzyme that, at an initial rate, liberates per minute an amount of TCA soluble product which gives the same colour with phenol reagent as one milli equivalent of tyrosine. A detailed description of the analytical method is given in a leaflet AF4 issued by Novo Industries.

Although some enzymes such as lysozyme solubilise peptidoglycan, we have found that it is desirable to employ, at least in initial enzyme digestion stages, enzyme compositions that effect little or no solubilisation of the peptidoglycan in the NPCM. The reason for this is that if the peptidoglycan is solubilised then separation of the insoluble HB polymer particles from the solubilised material tends to be more difficult. It is thought that the peptidoglycan forms a sort of mesh or "bag" enclosing agglomerates of the HB polymer particles. Such agglomerates can be separated from the aqueous medium more readily than de-agglomerated particles. The presence of peptidoglycan can be determined by measuring the diamino pimelic acid content of the insoluble residue containing the HB polymer.

As mentioned hereinbefore, solubilisation of NPCM may also be effected by the use of a surfactant as solubilising agent, preferably after a proteolytic enzyme digestion step. Solubilisation with a surfactant, e.g. an anionic surfactant such as a sulphated or sulphonated fatty acid, particularly sodium dodecyl sulphate, is preferably effected by heating the suspension, to which the surfactant has been added, to a temperature above 80° C. The amount of surfactant employed is preferably 10 to 200% by weight of the NPCM remaining in the suspension. The addition of a complexing agent such as ethylene diamine tetra-acetic acid to the surfactant may be advantageous in assisting solubilisation of NPCM.

We have found that in some cases where the surfactant treatment is conducted after enzymatic digestion, in particular where the heat treatment prior to enzyme digestion was not particularly severe e.g. where the temperature did not exceed 100° C., an emulsion may be formed on such surfactant treatment from which the solids can only be separated with difficulty. We have found that the addition of cationic flocculants or electrolytes to such emulsions are not particularly effective in assisting that separation. However acidification to a pH below 2, or the addition of an absorbent mineral such as Kieselguhr, can assist separation: acidification may however cause precipitation of some of the NPCM solubilised by the surfactant.

The insoluble residue remaining after the digestion step will comprise the HB polymer together with some residual, non-solubilised, NPCM.

The extent of solubilisation of the NPCM at any given stage is conveniently computed from the HB polymer content of the original cells and of the HB polymer-containing product obtained at that stage. For the purposes of this calculation it is assumed that there are no losses and that none of the HB polymer has been solubilised.

Thus, if the original cells contained $P_0\%$ by weight of HB polymer, and the product has a HB polymer content of $P_1\%$ by weight, then the percentage, N, of NPCM solubilised is given by $$N = \left[ 1 - \frac{P_o(100 - P_1)}{P_1(100 - P_o)} \right] \times 100$$

The heat treatment and digestion steps are preferably such that at least 50% by weight of the NPCM of the original cells is solubilised, and also such that the residue contains at least 70%, preferably at least 85%, by weight, of HB polymer.

The amount of digestion required to achieve this will of course depend on the original HB polymer content, $P_0$, of the micro-organism cells. The micro-organism is preferably cultivated under such conditions that the HB polymer content, $P_o$, is at least 50% by weight. However as mentioned hereinbefore, economic considerations may limit the HB content, $P_0$, of the cells to less than 80% by weight.

In a preferred aspect of the invention, after solubilisation of NPCM by enzymatic and/or surfactant digestion, the residual material is treated with hydrogen peroxide. Where the bulk of the proteinaceous NPCM has been solubilised by proteolytic enzymes, hydrogen peroxide treatment may effect little or no further solubilisation of residual NPCM but may be desirable to remove discoloration of the HB polymer-containing residue. Hydrogen peroxide treatment may also be beneficial by enabling the HB polymer-containing residue to be more readily separated, e.g. by filtration, from the aqueous medium.

In other cases, e.g. where proteolytic enzyme digestion has been used to solubilise only part of the proteinaceous NPCM, and/or where digestion with a surfactant has been employed, hydrogen peroxide treatment may effect removal of a further proportion of NPCM.

Where the NPCM of the HB polymer-containing residue comprises lipids, e.g. where no digestion with a phospholipase enzyme has been employed, lipids can be removed by washing the HB polymer-containing residue with a solvent, e.g. methanol, in which the lipids are soluble but the HB polymer is insoluble. Such a solvent washing step may also be desirable as a deodorising step.

By the above procedures an insoluble residue generally containing at least 70%, preferably at least 85% and in particular at least 90% by weight of HB polymer may be obtained.

As mentioned hereinbefore it is preferred not to effect significant solubilisation of the peptidoglycan. Accordingly preferred products contain at least 90% HB polymer and at least 1, particularly 1 to 3% by weight of peptidoglycan. Preferably such materials contain less than 6% by weight of proteinaceous material.

In some cases the product from the digestion step can be used as such, for example as a moulding material. Alternatively the HB polymer can be extracted by solvent extraction with a solvent for the HB polymer, e.g. a partially halogenated hydrocarbon such as methylene chloride, chloroform, or 1,2-dichloroethane. Since the residual proportion of NPCM is small, separation of the NPCM from syrups, e.g. by filtration, is far less onerous than in the direct solvent extraction processes and so more concentrated syrups, e.g. containing 5–15% by weight of polymer can be employed. Thus the proportion of extraction solvent required can be reduced with consequent reduced solvent loss through incomplete solvent recovery.

The invention is illustrated by the following examples in which all percentages are expressed by weight. In Examples 1 to 5 and 7 to 16, and 18 to 19 the suspensions employed were obtained by centrifugation of cultures of the *Alcaligenes eutrophus* NCIB 11599 grown by continuous fermentation under nitrogen limitation using glucose as a substrate.

EXAMPLE 1

In this example the suspension, containing 50 g/l of cells having a 3-hydroxybutyrate homopolymer (PHB) content of about 60%, was boiled under reflux at 100° C. for various periods of time. The suspensions were then cooled and tris(hydroxymethyl)amino methane hydrochloride was added as a buffer to give a buffer concentration of 50 mM. The buffered suspensions were then incubated for 1 hour at 55° C. and pH 8.2 with 1%, based on the original cell dry weight, of a proteolytic enzyme composition, "Alcalase" (Registered Trade Mark) 0.6 L supplied by Novo Industries and said, in sales literature issued by Novo Industries, to have an activity of 0.6 AU/g. This amount of "Alcalase" corresponds to about 1.5 AU per 100 g of NPCM in the original cells.

Samples of the resultant digested suspension were diluted with ice cold water and then centrifuged for 1–2 minutes at 20,000 g. The resultant centrifuged pellets were washed three times with water and then their protein contents determined by a colorimetric method based on that described by Lowry et al in J. Biol. Chem. 193 (1951) 265.

The results were as follows:

| Boiling time (min) | Protein content (%) | Comments |
|---|---|---|
| 1 | 7.7 | viscous suspension that formed a pellet on centrifugation only with difficulty. |
| 5 | 6.2 | less viscous suspension but still difficult to form a pellet. |
| 10 | 5.8 | mobile suspension that formed a pellet readily |
| 30 | 5.6 | |
| 60 | 5.5 | |

Comparison with protein determinations by amino acid analysis showed that the colorimetric method gave a value approximately 75% of that obtained by amino acid analysis.

EXAMPLE 2

The effectiveness of a heat treatment stage can also be assessed by measuring the rate of settling of a suspension after heat treatment, before any enzyme treatment.

The aqueous suspension employed contained 20 g/l of cells containing 72% PHB. The suspension was heat treated by heating for 5 minutes in an autoclave and then centrifuged on a strobe centrifuge at 1000 rpm. The height of the solids/liquid interface was measured after various centrifuging times.

| Autoclave temperature °C. | Solids/liquid interface height (cm) after centrifuging for t minutes. | | | | | | |
|---|---|---|---|---|---|---|---|
| | t = 0 | 3 | 5 | 10 | 15 | 20 | 30 |
| 100 | ~7 | — | 6.7 | 6.4 | 6.0 | 5.6 | 4.6 |
| 120 | ~7 | — | 6.0 | 4.8 | 3.0 | 1.3 | — |
| 140 | ~7 | <1 | — | — | — | — | — |

It is seen that the higher the temperature, the more readily the separation can be effected.

EXAMPLE 3

The procedure of Example 1 was repeated, using a suspension containing 50 g/l of cells of PHB content 52%. The boiling was conducted for 10 minutes. In order to remove phospholipids, after the "Alcalase" digestion, the suspension was incubated at 40° C., pH 8.6, for 1 hour with varying amounts of a phospholipase enzyme composition, "Lecitase" 100S (trademark) supplied by Novo Industries.

The protein content of the products, before and after "Lecitase" treatment were determined as in Example 1 and the residual phospholipid content was determined by solvent extracting the phospholipids and assaying the extract enzymatically. In the enzymatic assay procedure the enzyme phospholipase c was employed. This hydrolyses phosphatides other than phosphatidyl ethanolamine relatively slowly and so only about 50% of the phospholipids present is detected by this method. Accordingly in the following table the phosphadidyl ethanolamine content, rather than total phospholipids, is quoted.

By way of comparison the above procedure was repeated but omitting the "Alcalase" digestion.

| "Lecitase"* concentration (%) | "Alcalase" treatment | Product analysis (%) | | | NPCM solubilised (%)** |
|---|---|---|---|---|---|
| | | PHB | Protein | Phosphatidyl ethanolamine | |
| 0.025 | yes | 83 | 10.4 | 0.4 | 65 |
| 0.25 | yes | 88 | 11.0 | 0.1 | 75 |
| 0.19 | no | 62 | — | 0.4 | 21 |
| 1.9 | no | 65 | — | 0.2 | 27 |
| original cells | no | 52 | — | 2.2 | 0 |
| heat treated and "Alcalase" digested | yes | 79 | 12.9 | 1.5 | 56 |

*% by weight of original cell dry weight
**calculated from PHB contents of product and original cells.

It is seen that, although it enabled a low phosphatidyl ethanolamine level to be achieved, heat treatment plus "Lecitase" digestion alone, even when using a relatively large proportion of "Lecitase", was not able to solubilise sufficient NPCM to give a product containing more than 70% polymer. However, when used following "Alcalase" treatment, the "Lecitase" treatment enabled a significant increase in the purity of the polymer to be achieved, although the "Lecitase" effected solubilisation of only a little of the protein.

EXAMPLE 4

In this example different concentrations of the proteolytic enzyme, "Alcalase" 0.6 L, and different digestion times are compared.

The procedure of Example 1 was repeated using a boiling time of 1 hour followed by digestion with various amounts of "Alcalase" 0.6 L. Samples were taken at intervals from each digestion for protein analysis by the colorimetric method. The proportion of protein in the original cells that has been solubilised is quoted in the following table rather than the actual protein content of the products.

| Enzyme concentration | | Digestion time (min) | Proportion of original protein solubilised (%) |
|---|---|---|---|
| (%)* | (AU/100 g NPCM) | | |
| 0.43 | 0.6 | 10 | 27 |
| | | 20 | 34 |
| | | 30 | 33 |
| | | 60 | 38 |
| 0.64 | 1.0 | 10 | 32 |
| | | 20 | 41 |
| | | 30 | 42 |
| | | 60 | 46 |
| | | 10 | 35 |
| | | 20 | 44 |
| 0.75 | 1.1 | 30 | 51 |
| | | 60 | 52 |
| | | 10 | 38 |
| | | 20 | 46 |
| 1.0 | 1.5 | 30 | 53 |
| | | 60 | 57 |
| | | 10 | 48 |
| | | 20 | 53 |
| 1.2 | 1.8 | 30 | 58 |
| | | 60 | 58 |

*based on weight of original cells.

EXAMPLE 5

In this example the effect of a surfactant digestion is assessed.

The cell suspension employed was the same as that used in Example 3. The following treatments were employed.

A. Boiling under reflux at 100° C. for 1 hour.

B. Addition of 10%, based on the cell dry weight, of sodium dodecyl sulphate, followed by boiling under reflux at 100° C. for 1 hour.

C. As B, but with the addition of sufficient ethylene diamine tetraacetic acid to give a 5 mM solution prior to the boiling.

D. As A, followed by digestion for 1 hour at 55° C., pH 8.2 with 1%, based on the cell dry weight, of "Alcalase" 0.6 L.

E. As D, followed by B.

F. As D, followed by C.

In this example the protein content was assessed by amino acid analysis. The diamino pimelic acid content gives an indication of the residual peptidoglycan level—the peptidoglycan content is approximately five times the quoted diamino pimelic acid content.

| Treatment | | | Product analysis | | | | |
|---|---|---|---|---|---|---|---|
| Boiling | "Alcalase" digestion | Boiling with sodium dodecyl sulphate | PHB | Protein | D.P.A. | P.E. | N.A. |
| no | no | no | 52 | 25.4 | 0.24 | 2.2 | 5 |
| yes | no | no | 72 | 16.8 | 0.25 | 0.9 | 0.6 |
| no | no | yes | 93 | 4.4 | 0.24 | 0.4 | 0.28 |
| no | no | yes (+ EDTA) | 94 | 3.8 | 0.25 | 0.3 | <0.05 |
| yes | yes | no | 91 | 5.2 | 0.24 | 0.9 | 0.5 |
| yes | yes | yes | 96 | 2.5 | 0.25 | 0.4 | 0.06 |

-continued

| Treatment | | | Product analysis | | | | |
|---|---|---|---|---|---|---|---|
| Boiling | "Alcalase" digestion | Boiling with sodium dodecyl sulphate | PHB | Protein | D.P.A. | P.E. | N.A. |
| yes | yes | yes (+ EDTA) | 97 | 2.4 | 0.26 | 0.20 | <0.05 |

D.P.A. = diamino pimelic acid
P.E. = phosphatidyl ethanolamine
N.A. = nucleic acids
EDTA = ethylene diamine tetra-acetic acid It is seen that while the various treatments gave significantly reduced protein levels, the diaminopimelic acid content indicates that little of the peptidoglycan was solubilised.

In another experiment, a suspension containing 50 g/l of cells of PHB content 60%, was subjected to treatment F above, with similar results. Further digestion stages with "Alcalase" or sodium dodecyl sulphate after treatment F gave no significant improvement in product purity.

EXAMPLE 6

In this example the suspension employed contained 50 g/l of *Alcaligenes eutrophus* (NCIB 11599) cells containing 48% of a 3-hydroxybutyrate/3-hydroxyvalerate copolymer containing 10 mol % of 3-hydroxyvalerate units, obtained by centrifugation of a culture of the micro-organism grown by continuous fermentation under nitrogen limitation on a mixture of glucose and propionic acid as the substrate.

The procedure F of Example 5 was repeated but using a period of 10 minutes instead of 1 hour for the initial boiling prior to "Alcalase" digestion. After the sodium dodecyl sulphate digestion the product was divided into portions and centrifuged to give pellets.

One pellet was suspended in 50 mM phosphate buffer to which EDTA had been added to give an EDTA concentration of 1 mM. 0.1% based on the weight of the pellet, of egg white lysozyme (supplied by Sigma Chemicals) was added the the suspension digested for 1 hour at 20° C. and pH 6.5.

Another pellet was suspended in 50 mM acetic buffer + 1 mM EDTA and 0.1%, based on the weight of the pellet, of the cell wall lysing enzyme sold under the trademark "Novozyme" 234 (supplied by Novo Industries) was added and the suspension digested for 1 hour at 50° C., pH 4.5.

Another pellet was digested for 15 min in 0.1M sodium hydroxide at 20° C. This alkali digestion was also applied to the products resulting from the hysozyme and "Novozyme" digestions.

| Treatment | | | | Product analysis (%) | | |
|---|---|---|---|---|---|---|
| Boil, "Alcalase" digest, sodium dodecyl sulphate digest | lysozyme | "Novozyme" | Alkali | HB/HV copolymer | Protein* | DPA |
| yes | no | no | no | 86 | 6.7 | 0.5 |
| yes | no | no | yes | 91 | 6.9 | 0.5 |
| yes | yes | no | no | 90 | 6.0 | <0.03 |
| yes | yes | no | yes | 95 | 4.3 | <0.03 |
| yes | no | yes | no | 89 | 6.4 | 0.5 |
| yes | no | yes | yes | 89 | 6.2 | 0.5 |

*by amino acid analysis

It is seen that the lysozyme significantly reduced the diamino pimelic acid content. Alkali treatment and "Novozyme" had no significant affect on the diamino pimelic acid content but the alkali treatment when used alone or after lysozyme significantly improved the purity of the HB polymer.

EXAMPLES 7-11

In these examples the suspension contained 90 g/l of cells having a PHB content of 79%.

The suspension was heat treated by heating to 140° C. for 3 minutes in an autoclave by injection of steam under pressure. The suspension was then cooled and centrifuged.

Portions of the solid residue were re-suspended in water to give suspensions of solids content 50 g/l. To the suspensions there were then added commercial enzyme compositions and the suspensions were digested for 60 min at 50° C. at pH values (adjusted as necessary by addition of sodium hydroxide) recommended by the enzyme suppliers.

The insoluble residues were then separated from the aqueous media by centrifugation and washed with de-ionised water. The results are shown in the following table.

| Example | Enzyme | Enzyme concentration (g/l) | pH | PHB content of residue (%) | NPCM solubilised** (%) |
|---|---|---|---|---|---|
| 7 | "Protease" L330* | 0.5 | 8.5 | 93 | 72 |
| 8 | "Esparase" 8.0 L† | 0.5 | 8.5 | 89 | 54 |
| 9 | "Alcalase" 0.6 L† | 0.5 | 8.5 | 88 | 49 |
| 10 | "Neutrase" 0.5 L† | 0.5 | 7.0 | 87 | 44 |
| 11 | "Alcalase" 0.6 L† | 0.25 | 7.0 | 91 | 63 |

| Example | Enzyme | Enzyme concentration (g/l) | pH | PHB content of residue (%) | NPCM solubilised** (%) |
|---|---|---|---|---|---|
| | "Neutrase" 0.5 L⁺ | 0.25 | | | |

*(trademark) bacterial proteinase supplied by Miles UK
⁺(trademark) bacterial proteinase supplied by Novo Enzymes, UK
**calculated from PHB contents of product and original cells.

Further solubilisation of the NPCM in the products of Examples 9 and 10 could be effected by subjecting the residue to a further enzyme digestion and/or digestion with surfactant.

By comparison of Example 11 with Examples 9 and 10, it is seen that the use of the mixture of proteolytic enzymes gives superior NPCM solubilisation than an equivalent quantity of the individual enzymes.

EXAMPLE 12

The product of Example 11 was resuspended in water and digested at 50° C. and pH 7.0 for 60 min. with a further 0.25 g/l of "Neutrase" 0.5 L in admixture with 0.25 g/l of "Alcalase" 0.6 L. The residue was separated from the aqueous medium by centrifugation and washed with de-ionised water. The residue contained 96% PHB, corresponding to an overall NPCM solubilisation of 84%.

EXAMPLES 13-16

The procedure of Examples 7-11 was repeated using a suspension of cells having a PHB content of 75%, using various proteolytic enzyme compositions with the digestion being performed at pH 7 for 60 minutes at temperatures recommended by the enzyme suppliers. In each case the amount of enzyme composition employed was 1% based on the original cell dry weight.

| Example | Enzyme | Temperature °C. | PHB content of residue (%) | NPCM solubilised (%) |
|---|---|---|---|---|
| 13 | Bromelain concentrate | 55 | 89 | 63 |
| 14 | Papain 30,000 | 70 | 89 | 63 |
| 15 | "Allprotease" | 50 | 84 | 43 |
| 16 | "High T" | 32 | 80 | 25 |

The bromelain concentrate (activity 1295 BTU/g—derived from pineapple stems) and papain (activity 30,000 PU/mg—derived from carica papaya fruit) were both supplied by Miles Takamine of Elhart, Ind., USA. The "Allprotease" (trademark) and "High T" (trademark) were supplied by All-Tech of Lexington, Ky., USA: "Allprotease" is a mixture of fungal, bacterial, and plant enzymes while "High T" is derived from *Bacillus licheniformis*.

EXAMPLE 17

In this example the suspension employed was of cells of *Methlobacterium organophilum* NCIB 11483 obtained by batch cultivation on methanol as substrate under nitrogen limitation. The cells contained 17% PHB.

The procedure of Examples 7-16 was repeated using as the enzyme composition a mixture of 0.5% "Alcalase" 0.6 L and 0.5% "Neutrase" 0.5 L (both expressed as percentages of the original cell dry weight), a digestion time of 60 minutes, pH 7.0, and a temperature of 55° C. The product was subjected to further digestion steps, using the same conditions and a fresh enzyme charge for each digestion, with the product being centrifuged and resuspended in de-ionised water between each digestion.

The results were as follows:

| No. of digestions | PHB content of product (%) | Total NPCM solubilised (%) |
|---|---|---|
| 1 | 36 | 64 |
| 2 | 40 | 69 |
| 3 | 55 | 83 |

EXAMPLE 18

In this example the suspension contains 100 g/l of cells of PHB content 57%.

500 ml of the suspension was charged to a first stirred autoclave. A similar quantity of water was charged to a second stirred autoclave and heated under nitrogen pressure to 350° C. The first autoclave was pressurised with nitrogen to a pressure exceeding that in the second autoclave and then the contents of the first autoclave were forced into the second autoclave by the nitrogen pressure excess. The combined contents of the second autoclave were mixed vigorously for two minutes. The temperature of the combined contents of the second autoclave was approximately 170° C. but the applied pressure was sufficient to maintain the liquid state. The contents of the second autoclave were then forced by the nitrogen pressure into a collection vessel at atmospheric pressure.

The resulting product was centrifuged: the centrifuged pellet, was re-suspended in 500 ml of de-ionised water to which there was then added 0.5 g of "Alcalase" 0.6 L. The suspension was maintained at 55° C. and pH 7 for 30 minutes. After this time the suspension was centrifuged at 5000 g for 10 minutes. The centrifuged pellet was re-suspended in 500 ml of de-ionized water to which there was then added 0.5 g of "Lecitase" 100S. The suspension was maintained at pH 7, and 55° C., for 30 minutes. The suspension was then centrifuged at 5000 g for 10 minutes. The centrifuged pellet was then re-suspended in 500 ml of de-ionised water. 5 g, i.e. about 107% of the remaining NPCM, of sodium dodecyl sulphate were then added and the suspension heated for 1 hour at 100° C. The suspension was then centrifuged at 5000 g for 10 minutes to give a pellet which was then washed twice with de-ionised water, recovering the pellet between washes by centrifugation, and finally dried to give a brown product (Product A).

The above procedure was repeated but combining the "Alcalase" and "Lecitase" digestion steps, using for the digestion a mixture of 0.5 g of "Alcalase" and 0.5 g of "Lecitase".

| Treatment | | | | | | PHB content | |
|---|---|---|---|---|---|---|---|
| H | A | L | A+L | S | W | % | % NPCM solubilised* |
| x | x | x | x | x | x | 57 | 0 |
|   | x | x | x | x | x | 61 | 15 |
|   |   | x | x | x | x | 79 | 65 |
|   |   |   | x | x | x | 86 | 78 |
|   |   |   | x |   | x | 93 | 90 |
|   |   |   | x |   |   | 95 | 93 |
| x | x |   |   | x | x | 80 | 67 |
| x | x |   |   |   | x | 91 | 87 |
| x | x |   |   |   |   | 94 | 92 |

H = heat treatment
A = "Alcalase" digestion
L = "Lecitase" digestion
A + L = Simultaneous "Alcalase" and "Lecitase" digestion
S = sodium dodecyl sulphate digestion
W = final wash
*calculated from PHB contents of the product and original cells.

When the "Alcalase" digestion step was performed directly on the initial suspension, i.e. omitting the heat treatment stage, the suspension became extremely viscous and could not be stirred or further processed to separate the insoluble portion.

1 part of the brown product A mentioned above was extracted with 10 parts of methylene chloride under reflux and the syrup was then fltered. Despite the high viscosity of the syrup, standard techniques for syrup filtration as adopted in cellulose triacetate film manufacture could be employed since the proportion of NPCM to be removed was only about 0.5% of the syrup.

The filtered syrup could be cast to give a PHB film.

A portion of the syrup was added to petroleum ether to precipitate the HB polymer as a fine white powder B.

Samples of each of product A and Powder B were melt extruded by the following techniques:

A 3.5 g sample is charged to the barrel of a melt flow grader (Daventest, Welwyn, England) provided with a die having a circular orifice of 2 mm diameter and 8 mm land length. The barrel is maintained at 190° C. After a 5 minute warm-up period, a 10 kg load is applied to the piston, which has a weight of 0.16 kg. The melt flow time is the total time, including the 5 minute warm-up period, taken for a total of 2 g of the sample to be extruded through the die.

The melt flow times were as follows

| Product A | 10.5 min |
|---|---|
| Powder B | 8.0 min |

By way of comparison, the melt flow times of PHB samples separated from *Alcaligenes eutrophus* cells by a spray drying/lipid extraction/solvent extraction technique as described in EP-A-15123 are typically in the range 8 to 10 minutes. This demonstrates that the melt stability of the polymer either before or after the above methylene chloride extraction step is similar to that of polymer extracted by a direct solvent extraction route.

The product A had a weight average molecular weight of about 1,000,000 as measured by gel permeation chromatography.

By way of comparison extraction of PHB from a suspension, similr to that employed as the starting material in this example, by digesting for 30 min. at 40° C. with sodium hypochlorite (15% based on cell dry weight) gave a product of weight average molecular weight of only about 101,000 thus indicating that hypochlorite digestion gave severe degradation of the polymer.

EXAMPLE 19

In this example the initial suspension used was the same as that employed in Example 18. 500 ml of the suspension was heated to 80° C. by means of a steam heated coil immersed in the suspension and then the suspension was cooled to 55° C. The "Alcalase", "Lecitase", and sodium dodecyl sulphate treatments described in Example 18 were then performed in sequence.

The suspension became slightly viscous after "Alcalase" digestion but could still be stirred. The centrifugation stages after the "Alcalase" and "Lecitase" digestions however were more difficult, since the flocs were extremely delicate and gel-like pellets were obtained as opposed to the firm pellets obtained in Example 18. However, after the sodium dodecyl sulphate treatment a stable suspension was formed which could not be separated readily by centrifugation. To examine the settling characteristics of the suspension 20 ml portions thereof were placed in test tubes to provide a vertical column of suspension 6 cm high. Various additives were added to the suspension and the height of the solid/liquid interface observed after various periods of time. The results are shown in the following table.

| Additive | pH of modified suspension | Interface height (cm) after T hours | | | |
|---|---|---|---|---|---|
| | | T = 0 | T = 2 | T = 4 | T = 18 |
| none | 7.2 | — | — | — | 4.2 |
| 0.02 g "Aquafloc" 4051 | 7.2 | — | — | — | 3.0 |
| 0.02 g "Aquafloc" 4067 | 7.2 | — | — | — | 3.0 |
| 0.5 g CaCl$_2$ | 7.2 | — | — | 5.9 | 4.8 |
| 0.2 g Kieselguhr | 7.2 | — | 4.0 | 3.5 | 2.8 |
| HCl | 4.46 | — | — | 5.6 | 5.2 |
| HCl | 3.40 | — | — | 5.6 | 5.0 |
| HCl | 1.75 | — | 5.5 | 5.3 | 3.7 |
| HCl | 1.60 | — | 4.5 | 3.5 | 2.5 |

— = no interface

It is seen that whereas an electrolyte (CaCl$_2$) or cationic flocculants ("Aquafloc" 4051 or 4067) were ineffective, the addition of Kieselhuhr or sufficient HCl to reduce the pH to below 2 enabled settling to occur.

Low g centrifugation of similar suspension columns was also performed on the unmodified suspension and on the suspension acidified with HCl to pH 1.60.

The interface height after various times of centrifugation at 500 g is shown in the following table.

| Centrifugation Time (min) | Interface height (cm) | |
|---|---|---|
| | pH 7.2 | pH 1.6 |
| 0 | — | — |
| 2 | 5.9 | 5.6 |
| 3 | 5.9 | 4.8 |
| 4 | 5.8 | 4.1 |
| 5 | 5.7 | 3.6 |
| 10 | 5.1 | 2.4 |
| 15 | 4.3 | 1.9 |
| 20 | 3.6 | 1.6 |
| 30 | 2.8 | 1.4 |

EXAMPLE 20

*Alcaligenes eutrophus* (NCIB 11599) was batch cultured in an aqueous medium on a mixture of glucose and propionic acid under nitrogen limitation to give a culture containing 21 g/l of cells containing 71% of a 3-hydroxybutyrate (HB)/3-hydroxyvalerate (HV) copolymer having a HB:HV molar ratio of 4.9:1.

The culture was passed from the fermenter at a rate of 130 l/hr through a sterilizer maintained at 135° C. and then through a cooler at 70° C. and into a storage vessel. The residence time in the sterilizer was approximately 7 minutes.

The pH of the culture in the storage vessel was adjusted to pH 8 and then 0.21 g/l of "Alcalase" 0.6 L added when the temperature had fallen to 50° C. The mixture was left in the storage vessel overnight during which time the temperature of the mixture fell to 27° C. The mixture was then centrifuged: the solid residue had an HB copolymer content of 84%, corresponding to solubilisation of 53% of the NPCM. This residue was resuspended in water to give a suspension of 20 g/l solids content and then the suspension was divided into two portions which were separately treated.

A. To the first portion 0.2 g/l of "Alcalase" 0.6 L were added and the mixture digested at 55° C., pH 8, for 1 hour and then centrifuged. The HB copolymer content of the residue was 92% corresponding to solubilisation of 79% of the NPCM.

This residue was then suspended in water to give a solids content of approximately 260 g/l and digested with 500 ml/l of 10 vol. hydrogen peroxide for 2 hours at 80° C. The decolorised residue was separated by centrifugation, washed with water, and dried: the HB copolymer content of the residue was 92% indicating that the hydrogen peroxide treatment effected no further NPCM solubilisation.

B. To the second portion of the suspension 2 g/l of sodium dodecyl sulphate were added and the mixture boiled for 1 hour. The mixture was then centrifuged to give a residue having an HB copolymer content of 87% corresponding to solubilisation of 63% of the NPCM.

This residue was divided into two parts which were separately treated:

I. The first part of the residue was suspended in water to give a suspension of approximately 190 g/l solids content and digested with 500 ml/l of 10 vol. hydrogen peroxide for 2 hours at 80° C. The decolorised residue was separated by centrifugation, washed with water and dried. The dried residue had an HB copolymer content of 96% corresponding to an overall solubilisation of 90% of the NPCM.

II. The second part of the residue was washed with methanol and then water, and then separated by centrifugation. The residue had an HB copolymer content of 93% corresponding to solubilisation of 82% of the NPCM. This wet residue was resuspended in water to a solids content of 200 g/l and then digested with 10 vol. hydrogen peroxide at a concentration of 500 ml/l for 2 hours at 80° C. The resultant decolorised slurry was centrifuged to give a residue that was then washed with water and dried. The dried residue had an HB copolymer content of 98%, corresponding to solubilisation of 95% of the NPCM.

EXAMPLE 21

*Alcaligenes eutrophus* NCIB 11599 was batch cultured in an aqueous medium on a mixture of glucose and propionic acid under nitrogen limitation to give a suspension containing 45 g/l of cells containing 75% of an HB/HV copolymer having an HB/HV molar ratio of 4:1.

In this example enzyme and surfactant quantities are expressed as percentages based on the original cell dry weight.

The suspension was passed through a pipe where it was heated, by injection of steam, to 150° C. with a residence time at 150° C. of 20 sec. The resulting suspension was cooled to 70° C. and digested at that temperature for 2 hours at pH 7.5 with a mixture of 0.5% "Alcalase" 0.6 L and 0.5% "Neutrase" 0.5 L.

The resulting suspension was concentrated by centrifugation and then digested at 75° C. for 2 hours at pH 8.5 with 1% "Protease" L330.

The resulting suspension was concentrated by centrifugation and then 3% of sodium dodecyl sulphate was added and the suspension boiled under reflux at 100° C. for 2 hours.

The resulting suspension was then spray dired. The spray dried powder was washed with methanol under reflux, filtered and dried.

The HB polymer content at the various stages were as follows:

|  | HB polymer content of residue (%) | NPCM solubilised* (%) |
|---|---|---|
| After "Alcalase"/"Neutrase" digestion | 88 | 59 |
| After "Protease" digestion | 92 | 74 |
| After methanol wash | 93 | 77 |

*calculated from HB polymer contents of product and original cells.

We claim:

1. A process for the removal of non 3-hydroxybutyrate polymer cell material from bacterial microorganism cells containing a 3-hydroxybutyrate polymer comprising the steps of:
   (a) heating an aqueous suspension of said cells to a temperature above 80° C. so that said cells are lysed and digesting said lysed cells with at least one solubilizing agent selected from the group consisting of a proteolytic enzyme composition and a surfactant whereby said non-hydroxybutyrate polymer cell material in said cells is solubilized, wherein when said solubilizing agent is said proteolytic enzyme said heating takes place only prior to digestion; and
   (b) separating a water insoluble residue containing said 3-hydroxybutyrate polymer from a solution resulting from step (a).

2. A process according to claim 1 wherein said digesting step includes at least one stage wherein the solubilising agent is a proteolytic enzyme composition.

3. A process according to claim 2 wherein the suspension is heated to a temperature of at least 100° C. prior to the proteolytic enzyme digestion stage.

4. A process according to claim 2 wherein the digesting step includes at least one stage wherein the solubilising agent is a surfactant, the surfactant digestion being effected after digestion with the proteolytic enzyme.

5. A process according to claim 2 wherein the digesting step includes at least one stage wherein the solubilising agent is a phospholipase.

6. A process according to claim 2 wherein the enzyme digestion is effected at a temperature below 80° C.

7. A process according to claim 1 wherein the digesting step includes at least one stage wherein the solubilising agent is a surfactant and the surfactant digestion is effected at a temperature of at least 80° C.

8. A process according to claim 1 wherein at least one digestion stage the solubilising agent is a surfactant in admixture with ethylene diamine tetra-acetic acid.

9. A process according to claim 1 wherein after the digesting step, the residue is treted with hydrogen peroxide.

10. A process according to claim 1 wherein the separated insoluble residue comprises at least 90% by weight of 3-hydroxybutyrate polymer and at least 1% by weight of peptidoglycan.

* * * * *